US00PP36684P2

(12) United States Plant Patent
Kerley et al.

(10) Patent No.: US PP36,684 P2
(45) Date of Patent: May 13, 2025

(54) ***PRIMULA* PLANT NAMED 'KERANNAWEAVE'**

(50) Latin Name: *Primula elatior*
Varietal Denomination: KERANNAWEAVE

(71) Applicant: Kerley & Co, Willingham (GB)

(72) Inventors: David William Kerley, Over (GB); Timothy Edward Kerley, Willingham (GB)

(73) Assignee: Kerley & Co Ltd (GB)

( * ) Notice: Subject to any disclaimer, the term of this patent is extended or adjusted under 35 U.S.C. 154(b) by 0 days.

(21) Appl. No.: 18/799,767

(22) Filed: Aug. 9, 2024

(51) Int. Cl.
*A01H 6/00* (2018.01)
*A01H 5/02* (2018.01)

(52) U.S. Cl.
USPC ..... Plt./472

(58) Field of Classification Search
USPC ..... Plt./472
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Primula* plant named 'KERANNAWEAVE' is described, characterized by abundant, fully-double maroon flowers with an irregular gold rim. Plants have compact, uniform habits. The new variety is a *Primula*, normally used as an ornamental garden or landscape plant.

2 Drawing Sheets

Figure 1:
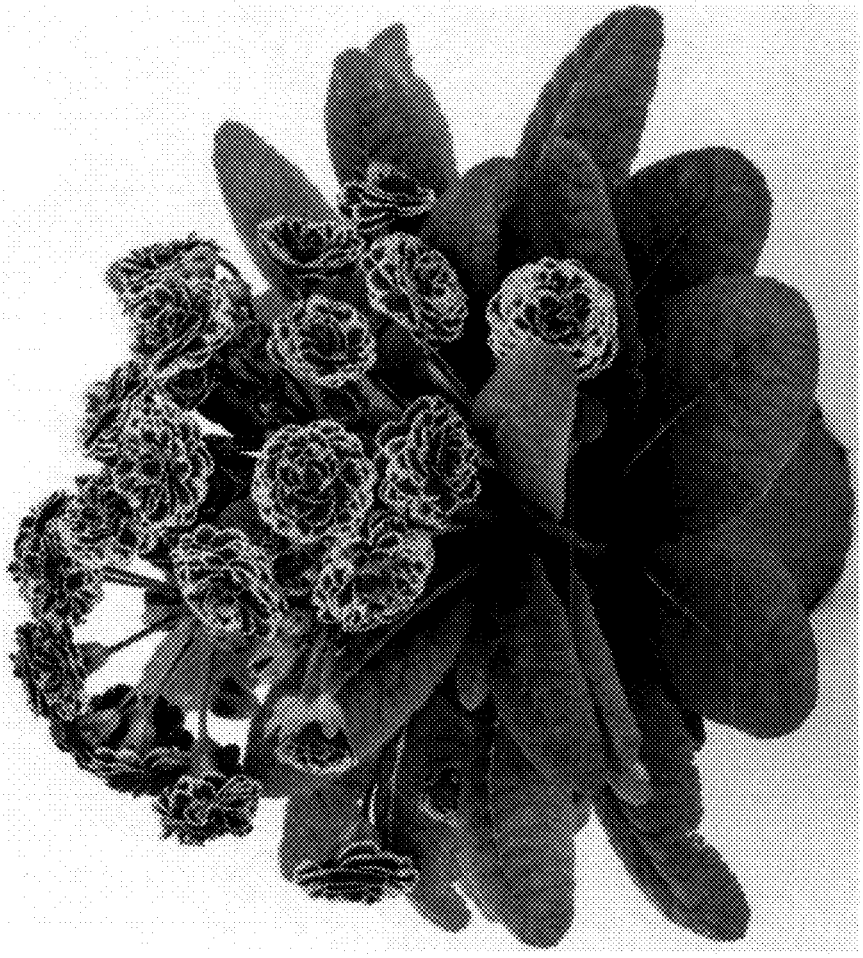

Latin name of the genus and species: *Primula elatior.*
Variety denomination: 'KERANNAWEAVE'.

BACKGROUND OF THE INVENTION

The new cultivar is the product of a planned breeding program under the direction of the inventors. *Primula* 'KERANNAWEAVE' resulted from the crossing of the seed parent, an unpatented, unnamed, proprietary variety of *Primula*, and the pollen parent, a different unnamed, unpatented, proprietary variety of *Primula*. The crossing resulting in the new variety was made in April of 2016 at a research greenhouse in Cambridge, United Kingdom. Selection of the new variety 'KERANNAWEAVE' was made in March of 2017, by the inventor at a research greenhouse located in Cambridge, United Kingdom.

Asexual reproduction of the new cultivar 'KERANNAWEAVE' was first performed in Cambridge, the United Kingdom during May of 2017, by tissue culture. This and subsequent propagation has shown that the unique features of this cultivar are stable and reproduced true to type in successive generations.

SUMMARY OF THE INVENTION

The cultivar 'KERANNAWEAVE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERANNAWEAVE'. These characteristics in combination distinguish 'KERANNAWEAVE' as a new and distinct *Primula* cultivar:

1. Double flowers.
2. Maroon flower color with irregular gold rim.
3. Abundant flowering.

4. Compact plant habit.

PARENT COMPARISONS

Plants of the new cultivar 'KERANNAWEAVE' are similar to plants of the seed parent, in most horticultural characteristics. However, plants of the new cultivar differ in the following ways:

1. Flowers of the new variety are double, while flowers of the seed parent are single.
2. Flowers of the new variety are sterile, while flowers of the seed parent are fertile.

Plants of the new cultivar 'KERANNAWEAVE' are similar to plants of the pollen parent, in most horticultural characteristics. However, plants of the new cultivar differ in the following ways:

1. Flowers of the new variety are double, while flowers of the pollen parent are single.
2. Flowers of the new variety are sterile, while flowers of the pollen parent are fertile.

COMMERCIAL COMPARISONS

Plants of the new variety can be compared to plants of the *Primula* cultivar 'Elisabeth Killelay', unpatented. Plants of the new *Primula* differed from plants of the cultivar 'Elisabeth Killelay' in the following characteristics:

1. Flowers of the new variety are larger than flowers of this comparator.
2. Flower rim pattern of the new variety is more irregular than the flower rim pattern of this comparator.
3. Plants of the new variety are less compact than plants of this comparator.
4. Plants of the new variety are more vigorous than plants of this comparator.
5. Plants of the new variety are taller than plants of this comparator.

Plants of the new variety can be compared to plants of the *Primula* cultivar 'Pollyanna Touch of Gold', unpatented. Plants of the new *Primula* differed from plants of the cultivar 'Pollyanna Touch of Gold' in the following characteristics:

1. Flowers of the new variety are smaller than flowers of this comparator.
2. Petals of the new variety have a gold stripe down the middle, while petals of this comparator do not.
3. Plants of the new variety are more vigorous than plants of this comparator.

BRIEF DESCRIPTION OF THE PHOTOGRAPHS

The accompanying photograph in FIG. 1 illustrates in full color a typical plant of 'KERANNAWEAVE' grown in Over, Cambridge, United Kingdom, in a glass-covered greenhouse. This plant was about 7 months old when the photographs were taken. During the production of the plants, day temperatures ranged from 5° C. to 15° C. and night temperatures ranged from 2° C. to 12° C.

Figure 2:
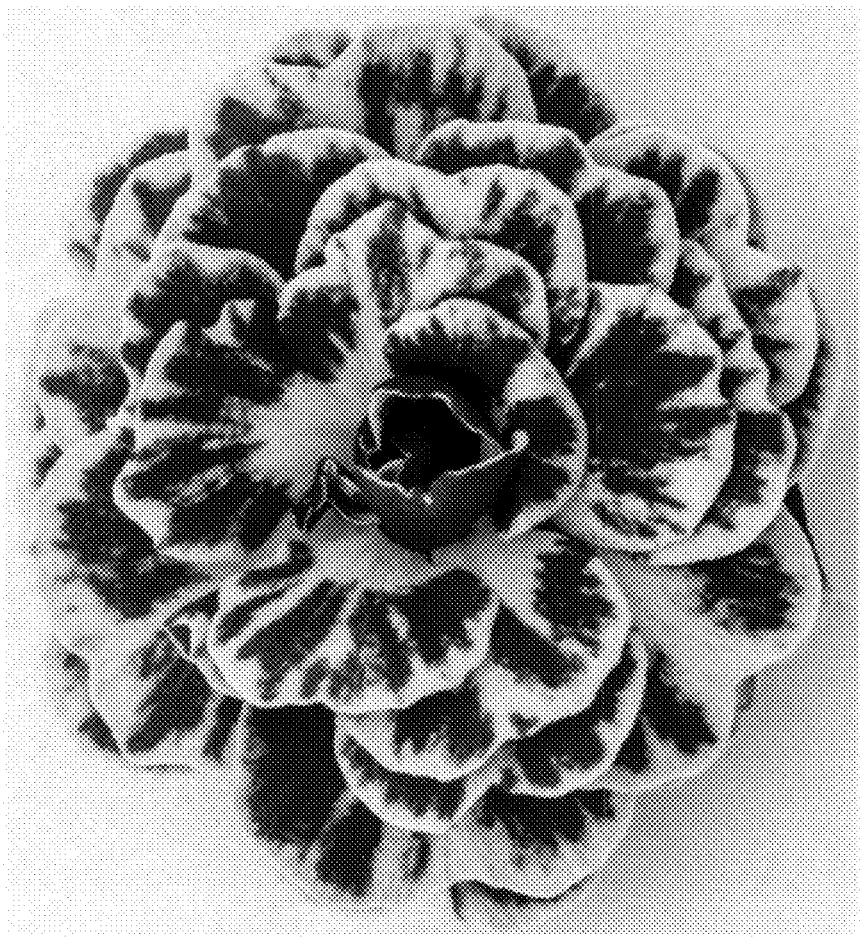

FIG. 2 illustrates a close up of a typical flower of 'KERANNAWEAVE'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2015 except where general terms of ordinary dictionary significance are used. The following observations and measurements describe 'KERANNAWEAVE' plants at approximately 6 months old grown in a greenhouse in Cambridge, United Kingdom. During the production of the plants, day temperatures ranged from 1.5° C. to 25° C. and night temperatures ranged from 1.5° C. to 15° C. No chemical or photoperiodic treatments were given. Measurements were taken during Spring and numerical values represent averages of typical flowering types.

Botanical classification: *Primula elatior* 'KERANNAWEAVE'.

PROPAGATION

Method: Tissue culture.

Time to produce a rooted plant: About 6 weeks at 20° C.

Root description: Fibrous, freely branching, colored nearest to RHS White 155A.

PLANT

Plant form/habit: Upright, compact and uniform, with flowers born on umbels above foliage.

Height: 23 cm.

Plant spread: 24.5 cm.

Branching characteristics: No branches, foliage emerges basally.

Vigor: Vigorous.

FOLIAGE

Leaf:

*Arrangement*.—Basal, simple.

*Length*.—12.4 cm.

*Width*.—5.5 cm.

*Shape*.—Oblanceolate.

*Apex*.—Obtuse.

*Base*.—Acute.

*Margin*.—Slightly crenate, irregular, undulating.

*Texture of top surface*.—Rugose.

*Texture of bottom surface*.—Rugose with prominent venation.

*Color*.—Developing foliage upper side: RHS Yellow-Green 144A. Developing foliage under side: RHS Yellow-Green 144B. Mature foliage upper side: Near RHS Yellow-Green 146A. Mature foliage under side: RHS Yellow-Green 146B.

*Venation*.—Type: Pinnate. Venation color upper side: RHS Yellow-Green 195C. Venation color under side: RHS Yellow-Green 195B.

Petiole:

*Length*.—0.7 cm.

*Diameter*.—0.4 cm.

*Strength*.—Medium.

*Color*.—Upper Surface: Near RHS Yellow-Green 194D with a slight blush of Purple-Pink 186D towards the base. Lower Surface: Near RHS Yellow-Green 194D with a hint of Purple-Pink 186D at the base.

*Texture upper surfaces*.—Slightly hirsute.

*Texture lower surfaces*.—Slightly hirsute.

FLOWER

Bloom period: Recurrent flowering during the Spring under United Kingdom outdoor conditions.

Flower type/habit: Umbel with rounded double flowers born on strong, upright stems. Flowers face upright and outward. Freely flowering habit.

Persistence: Persistent.

Fragrance: None.

Flowers per inflorescence: 10 to 18 flowers and buds per plant. 9 to 12 flower stems per plant.

Inflorescence height: 18.5 cm.

Inflorescence diameter: 11.5 cm.

Flower bud:

*Height*.—1.3 cm.

*Diameter*.—0.69 cm.

*Shape*.—Ovoid.

*Color*.—Near RHS Red 53A, with a hint of Yellow 162D at outer edge.

*Texture*.—Glabrous.

Individual flower:

*Diameter*.—3.5 cm.

*Depth*.—2.5 cm.

Petals:

*Quantity*.—About 18 per flower, in several concentric whorls.

*Length* (*including tube*).—2.3 cm.

*Width*.—1.7 cm.

*Shape*.—Obcordate.

*Apex*.—Emarginate.

*Margin*.—Mostly entire.

*Texture, upper and lower surfaces*.—Glabrous.

*Longevity*.—9 to 10 days.

*Color*.—Developing petals, upper surface: RHS Red 53A, with a rim of Yellow 161C. Rim is irregular, narrow at petal base and becomes wide at emarginate apex and extends down the middle of the petal, giving the impression of a band of 161C down the middle of the petal. Developing petals, lower surface: Near RHS Red 53A, with a hint of Yellow 161D on outer edge. Basal eye near Yellow 9A. Mature petals, upper surface: RHS Red 53A, with a rim of Yellow 161C. Rim is irregular, narrow at petal base and becomes wide at emarginate apex and extends down the middle of the petal, giving the impression of a band of 161C down the middle of the petal. Mature petals, lower surface: Near RHS Red 53A, with a slight hint of Yellow 161D at rim. Near Yellow 1A at the base.

Flower throat:
*Diameter.*—0.6 cm.
*Texture.*—Glabrous.
*Color.*—Near RHS Yellow 1C.

Flower tube:
*Diameter.*—0.4 cm.
*Texture.*—Glabrous.
*Color.*—Near RHS Yellow 1D.

Sepals:
*Quantity.*—5 in a single whorl; fused at base.
*Length.*—1.5 cm.
*Width.*—0.5 cm.
*Shape.*—Rhomboid.
*Apex.*—Acute.
*Margin.*—Entire.
*Texture upper surface.*—Glabrous.
*Texture lower surface.*—Glabrous; slightly hirsute on central vein.
*Color, upper surface.*—RHS Yellow-Green 144A.
*Color, lower surface.*—RHS Yellow-Green 147B.

Peduncle:
*Length.*—15.8 cm.
*Diameter.*—0.5 cm.
*Orientation.*—Upright and slightly outward.
*Strength.*—Medium.
*Color.*—Near RHS Yellow-Green 195B at the base, changing to near Red-Orange 177D at the apex.
*Texture.*—Pubescent.

Pedicels:
*Length.*—2.9 cm.
*Diameter.*—0.2 cm.
*Orientation.*—Upwards and outwards.
*Strength.*—Medium.
*Texture.*—Pubescent.
*Color.*—Near RHS Gray-Yellow 199D.

Floral bracts:
*Quantity per pedicel.*—One.
*Length.*—1.2 cm.
*Width.*—0.3 cm.
*Shape.*—Narrow lanceolate.
*Texture.*—Smooth.
*Apex.*—Acute.
*Color.*—Near RHS Yellow-Green 144A.

REPRODUCTIVE ORGANS

Development of reproductive organs has not been observed.

OTHER CHARACTERISTICS

Disease resistance and pest: Plants of the new *Primula* have not been noted to be resistant nor susceptible to pathogens and pests common to *Primula*.

Temperature tolerance: Plants of the new *Primula* have been observed to have tolerated temperatures from about −5° to 28° C.

Fruit/seed production: Fruit and seed production not observed; flowers are sterile.

What is claimed is:

1. A new and distinct cultivar of *Primula* plant named 'KERANNAWEAVE' as herein illustrated and described.

* * * * *